US008729282B2

(12) United States Patent
Postma et al.

(10) Patent No.: US 8,729,282 B2
(45) Date of Patent: *May 20, 2014

(54) PROCESS FOR THE MANUFACTURE OF A 1,2-EPOXIDE

(75) Inventors: Ron Postma, Vondelingenplaat (NL); Prasad Muppa, Vondelingenplaat (NL)

(73) Assignee: Momentive Specialty Chemicals Inc., Columbus, OH (US)

( * ) Notice: Subject to any disclaimer, the term of this patent is extended or adjusted under 35 U.S.C. 154(b) by 208 days.

This patent is subject to a terminal disclaimer.

(21) Appl. No.: 13/056,793

(22) PCT Filed: Jul. 9, 2009

(86) PCT No.: PCT/EP2009/004977
§ 371 (c)(1),
(2), (4) Date: Jan. 31, 2011

(87) PCT Pub. No.: WO2010/012361
PCT Pub. Date: Feb. 4, 2010

(65) Prior Publication Data
US 2011/0137054 A1    Jun. 9, 2011

(30) Foreign Application Priority Data

Aug. 1, 2008  (EP) .................................... 08075680

(51) Int. Cl.
*C07D 301/12* (2006.01)
(52) U.S. Cl.
USPC ........................................................ 549/531
(58) Field of Classification Search
USPC ........................................................ 549/531
See application file for complete search history.

(56) References Cited

U.S. PATENT DOCUMENTS

| | | | |
|---|---|---|---|
| 4,021,454 A | 5/1977 | Wulff et al. |
| 4,038,291 A | 7/1977 | Gipson |
| 4,127,594 A | 11/1978 | Anderson et al. |
| 4,824,976 A | 4/1989 | Clerici et al. |
| 4,937,216 A | 6/1990 | Clerici et al. |
| 4,973,718 A | 11/1990 | Buchler |
| 5,153,161 A | 10/1992 | Kerschner et al. |
| 5,155,274 A | 10/1992 | Herrmann et al. |
| 5,194,416 A | 3/1993 | Jureller et al. |
| 5,256,779 A | 10/1993 | Kerschner |
| 5,274,147 A | 12/1993 | Kerschner et al. |
| 5,284,944 A | 2/1994 | Madison et al. |
| 5,329,024 A | 7/1994 | Jureller et al. |
| 5,429,769 A | 7/1995 | Nicholson et al. |
| 5,466,836 A | 11/1995 | Jubin, Jr. |
| 5,516,738 A * | 5/1996 | Jureller et al. ................ 502/155 |
| 5,532,389 A | 7/1996 | Trent et al. |
| 5,681,789 A | 10/1997 | Saxton et al. |
| 5,833,755 A | 11/1998 | Schlon et al. |
| 5,840,934 A | 11/1998 | Goto et al. |
| 5,973,171 A | 10/1999 | Cochran et al. |
| 6,037,484 A | 3/2000 | Grey |
| 6,054,407 A | 4/2000 | Schulz et al. |
| 6,087,513 A | 7/2000 | Liao et al. |
| 6,187,935 B1 | 2/2001 | Gosselin et al. |
| 6,288,248 B1 | 9/2001 | Strebelle |
| 6,300,506 B1 | 10/2001 | Paparatto et al. |
| 6,350,888 B1 | 2/2002 | Strebelle et al. |
| 6,380,407 B1 | 4/2002 | Catinat et al. |
| 6,500,968 B2 | 12/2002 | Zhou et al. |
| 6,500,969 B1 | 12/2002 | Zhou et al. |
| 6,541,648 B1 | 4/2003 | Paparatto et al. |
| 6,590,112 B1 | 7/2003 | Catinat et al. |
| 6,596,881 B2 | 7/2003 | Haas et al. |
| 6,596,883 B2 | 7/2003 | Hofen et al. |
| 6,624,318 B1 | 9/2003 | Muller et al. |
| 6,673,950 B1 | 1/2004 | Teles et al. |
| 6,815,552 B2 | 11/2004 | Strebelle et al. |
| 7,141,683 B2 | 11/2006 | Haas et al. |
| 7,161,000 B2 | 1/2007 | Higashimura et al. |
| 7,161,005 B2 | 1/2007 | Schlingloff et al. |
| 7,205,419 B2 | 4/2007 | Strebelle et al. |
| 7,320,779 B2 | 1/2008 | Strebelle et al. |
| 7,323,578 B2 | 1/2008 | Catinat et al. |
| 7,541,479 B1 | 6/2009 | Chang et al. |
| 7,722,847 B2 | 5/2010 | Haas et al. |
| 7,981,391 B2 | 7/2011 | Haas et al. |
| 2001/0012909 A1 | 8/2001 | Mizuno |
| 2001/0025695 A1 | 10/2001 | Patt et al. |
| 2002/0010120 A1 | 1/2002 | Hage et al. |

(Continued)

FOREIGN PATENT DOCUMENTS

CN    1456582 A1    11/2003
CN    1900071        1/2007

(Continued)

OTHER PUBLICATIONS

Aldrich, Catalog Handbook of Fine Chemicals, 1998-1999, p. 497.*

(Continued)

*Primary Examiner* — Taylor Victor Oh

(57) ABSTRACT

The invention relates to a process for the manufacture of a 1,2-epoxide by catalytic oxidation of a terminal olefin with hydrogen peroxide wherein the catalytic oxidation is performed in a biphasic system comprising an organic phase and an aqueous reaction medium, wherein a water-soluble manganese complex is used as oxidation catalyst, wherein a terminal olefin is used with a solubility at 20° C. of at least 0.01 to 100 g in 1 liter water, and wherein the molar ratio of terminal olefin to hydrogen peroxide is in the range of from 1:0.1 to 1:2.

25 Claims, No Drawings

(56) References Cited

U.S. PATENT DOCUMENTS

| | | |
|---|---|---|
| 2002/0106320 A1 | 8/2002 | Zhou et al. |
| 2003/0035771 A1 | 2/2003 | Hasenzahl |
| 2003/0055293 A1 | 3/2003 | Wurziger et al. |
| 2003/0078160 A1 | 4/2003 | Hasenzahl et al. |
| 2003/0103894 A1 | 6/2003 | Hasenzahl et al. |
| 2003/0109726 A1 | 6/2003 | Balthasart |
| 2003/0144535 A1 | 7/2003 | Teles et al. |
| 2003/0158431 A1 | 8/2003 | Balthasart et al. |
| 2003/0187285 A1 | 10/2003 | Balthasart |
| 2003/0232004 A1 | 12/2003 | Zhou et al. |
| 2004/0039216 A1 | 2/2004 | Balthasart |
| 2004/0054200 A1 | 3/2004 | Paparatto et al. |
| 2004/0068128 A1 | 4/2004 | Teles et al. |
| 2004/0142843 A1 | 7/2004 | Schlingloff et al. |
| 2004/0151658 A1 | 8/2004 | Escrig et al. |
| 2004/0181081 A1 | 9/2004 | Forlin et al. |
| 2005/0065378 A1 | 3/2005 | Bosch et al. |
| 2005/0222440 A1 | 10/2005 | Kahn et al. |
| 2005/0240038 A1 | 10/2005 | Gobbel et al. |
| 2005/0250955 A1 | 11/2005 | Gobbel et al. |
| 2006/0025637 A1 | 2/2006 | Babler et al. |
| 2006/0041150 A1 | 2/2006 | Catinat et al. |
| 2006/0058539 A1 | 3/2006 | Babler et al. |
| 2006/0167288 A1 | 7/2006 | Strebelle et al. |
| 2006/0216216 A1 | 9/2006 | Bassler et al. |
| 2006/0264633 A1 | 11/2006 | Schlingloff et al. |
| 2006/0277687 A1 | 12/2006 | Buhler et al. |
| 2007/0142651 A1 | 6/2007 | Le-Khac et al. |
| 2008/0103319 A1 | 5/2008 | Miller |
| 2008/0262225 A1 | 10/2008 | Schlingloff et al. |
| 2009/0029168 A1 | 1/2009 | Butters et al. |
| 2009/0068282 A1 | 3/2009 | Schlingloff et al. |
| 2009/0149666 A1 | 6/2009 | Buhler et al. |
| 2010/0029848 A1 | 2/2010 | Forlin et al. |
| 2010/0056814 A1 | 3/2010 | Chang et al. |
| 2010/0094031 A1 | 4/2010 | Trent et al. |
| 2010/0113808 A1 | 5/2010 | Liebens et al. |
| 2010/0168379 A1 | 7/2010 | Krafft et al. |
| 2010/0179300 A1 | 7/2010 | Boulos et al. |
| 2010/0180802 A1 | 7/2010 | Gumlich et al. |
| 2010/0197947 A1 | 8/2010 | Narahara et al. |
| 2010/0204494 A1 | 8/2010 | Hatano |
| 2010/0331557 A1 | 12/2010 | Strebelle et al. |
| 2011/0054197 A1 | 3/2011 | Hofen et al. |
| 2012/0130095 A1 | 5/2012 | Crampton et al. |
| 2012/0130096 A1 | 5/2012 | Crampton et al. |

FOREIGN PATENT DOCUMENTS

| | | |
|---|---|---|
| CN | 100516056 C | 7/2009 |
| CN | 100545167 C | 9/2009 |
| CN | 101665474 B | 9/2009 |
| CN | 1931848 B | 5/2010 |
| CN | 201713456 U | 1/2011 |
| CN | 101993423 A | 3/2011 |
| CN | 101293882 B | 4/2011 |
| DE | 19923121 | 11/2000 |
| EP | 0458397 | 5/1991 |
| EP | 0458398 | 11/1991 |
| EP | 0618202 A1 | 10/1994 |
| EP | 0936219 A1 | 8/1999 |
| EP | 1115714 B1 | 5/2002 |
| EP | 1403219 | 3/2004 |
| EP | 1883730 | 2/2008 |
| EP | 2149570 A1 | 2/2010 |
| EP | 2402087 | 1/2012 |
| ES | 2336746 B1 | 1/2011 |
| JP | 2000-302766 | 10/2000 |
| JP | 2001-002662 | 1/2001 |
| JP | 2002145872 | 5/2002 |
| JP | 2005-154340 | 6/2005 |
| PL | 174464 B1 | 7/1998 |
| TW | 305831 | 6/1995 |
| TW | 200823183 | 6/2008 |
| WO | WO 99/23052 | 5/1999 |
| WO | WO 00/02872 | 1/2000 |
| WO | WO 00/76989 | 12/2000 |
| WO | WO 02/00634 | 1/2002 |
| WO | WO 03/018567 | 3/2003 |
| WO | WO 2004/028962 | 4/2004 |
| WO | WO 2004/029032 | 4/2004 |
| WO | WO 2004/048353 A1 | 6/2004 |
| WO | WO 2004/074268 | 9/2004 |
| WO | WO 2005/095370 A1 | 10/2005 |
| WO | WO 2007/046960 | 4/2007 |
| WO | WO 2008/078861 | 7/2008 |
| WO | WO 2008/078861 A1 | 7/2008 |
| WO | WO 2008/087657 | 7/2008 |
| WO | WO 2008/087657 A2 | 7/2008 |
| WO | WO 2008/098921 | 8/2008 |
| WO | WO 2009/063487 | 5/2009 |
| WO | WO 2009/063487 A2 | 5/2009 |
| WO | WO 2009/129355 | 10/2009 |
| WO | WO 2010/010003 | 1/2010 |
| WO | WO 2011/032666 | 3/2011 |

OTHER PUBLICATIONS

P.L. Alsters et al., "Fine-Tuning and Recycling of Homogeneous Tungstate and Polytungstate Epoxidation Catalysts", Mechanisms in Homogeneous and Heterogeneous Expoxidation Catalysis (2008) 415-428, Elsevier B.V. and Technology.

I.W.C.E. Arends et al., "Recent developments in selective catalytic epoxidations with H2O2", Topics in Catalysis, vol. 19, No. 1 (2002) 133-141.

T.H. Bennur et al., "Benzylic oxidation with H2O2 catalyzed by Mn complexes of N,N',N-trimelthyl-1,4,7-triazacyclononane: spectroscopic investigations of the active Mn Species", Journal of Molecular Catalysis A: Chemical 185 (2002) 71-80.

N.O. Brace et al., "Hydrophobic Compounds and Polymers from Long Chain Alkanamide-Formaldehyde Condensation Reactions", Journal of Organic Chemistry (1961) vol. 26, 5176-5180.

J. Brinksma et al., "Homogeneous cis-dihydroxylation and epoxidation of olefins with high H2O2 efficiency by mixed manganese/ activated carbonyl catalyst system", Tetrahedron Letters 43 (2002) 5619-2622.

A.M. d'A. Rocha Gonsalves et al., "On the mechanism of carboxylic acid co-catalyst assisted metalloporphyrin oxidations" Journal of Molecular Catalysis A: Chemical 168 (2001) 25-32.

J.W. De Boer et al., "The role of salicylic acid, L-ascorbic acid, and oxalic acid in promoting the oxidation of alkenes with H2O2 catalysed by [MnIV2(O)3(tmtacn)2]2+", Royal Society of Chemistry, Dalton Transactions (2008) 6283-6295.

J.W. De Boer, "cis-Dihydroxylation and Epoxidation of Alkenes by Manganese Catalysts Selectivity, Reactivity and Mechanism", Feb. 22, 2008, Dissertation, University of Groningen, PrintPartners lpskamp BV, Enschede, the Netherlands.

D.E. De Vos et al., "Highly selective olefin epoxidation with manganese triazacyclononane compleces:Impact of ligand substitution", Journal of Oganometallc Chemistry 520 (1996) 195-200.

D.E. E Vos et al., "Selective Alkene Oxidation with H2O2 and a Heterogenized Mn Catalyst: Epoxidation and a New Entry to Vicinal cis-Diols", Angew. Chem. Int. Ed. 38, No. 7 (1999) 980-983.

D.E. De Vos et al., "Epoxidation of Terminal or Electron-deflcient Olefins with H2O2, catalysed by Mn-trimethyltriazacyclonane Complexes in the Presence of an Oxalate Buffer", Tetrahedron Letters 39 (1998) 3221-3224.

D.E. De Vos et al., "Highly selective epoxidation of alkenes and styrenes with H2O2 and manganese complexes of the cyclic triamine 1,4,7-trimethyl-1,4,7-triazacyclononane", Chem. Commun. (1996) 917-918.

F.C. Frostick Jr. et al., "Synthesis of Some Vinyl Monomers by Epoxidation with Peracetic Acid", by J. Am. Chem. Soc. 81 (1958) 3350-3356.

A. Grenz et al., "Synthesis and application of novel catalytically active polymers containing 1,4,7-triazacyclononanes", Chem. Commun. (2001) No. 18, 1726-1727 (Cambridge, England).

(56) References Cited

OTHER PUBLICATIONS

R. Hage et al., "Bleach and oxidation catalysis by manganese-1,4,7-triazacylononane complexes and hydrogen peroxide", Journal of Molecular Catalysis A: Chemical 251 (2006) 150-158.

N. Hoffman et al., "Liquid-Liquid Biphasic, Platinum-Catalyzed Hydrosilylation of AllyL Chloride with Trichlorosilane Using an Liquid Catalyst Phase in a Continuous Loop Reactor", Adv. Synth. Catal. (2008) 350, 2599-2609.

E. Kaczmarczyk et al., "Selective epoxidation of 1,4-bis(allyloxy)butane to 1-allyloxy-glycidoloxybutane in the presense of ionic liquids", Journal of Molecular Catalysis A: Chemical 265 (2007) 148-152.

E. Kaczmarczyk et al., "Epoxidation of 1,4-bis(allyloxy)butane by hydrogen peroxide using phase transfer catalysis", Journal of Molecular Catalysis A: Chemical 244 (2006) 173-178.

E. Kaczmarczyk et al., "Epoxidation of 1,4-diallyloxybutane to 1-allyloxy-4-glycidyloxybutane by the method of phase transder catalysis", Journal of Molecular Catalysis A: Chemical 235 (2005) 52-56.

R. Mbeleck et al. "Stability and recycling of polymer-supported Mo(VI) alkene epoxidation catalysts", Reactive & Funcational Polymers 67 (2007) 1448-1457, Elsevier Science Publishers BV, Netherlands.

A. Murphy et al., "Ligand and pH Influence on Manganese-Mediated Peracetic Acid Epoxidation of Terminal Olefins", Organic Letters, (2004) vol. 6 No. 18, 3119-3122.

L. Ningning et al., "Epoxidation of Various Functionalized Olefins by a Ti-MWW/H2O2 Catalytic System", Chin J Catal (2008) vol. 29 Issue 2, 102-104.

G.V. Nizova et al., "Hydrocarbon Oxidations with Hydrogen Peroxide Catalyzed by a Soluble Polymer-Bound Manganese(IV) Complex with 1,4,7-Triazacyclononane", Adv. Synth. Catal. (2002) 344, No. 8, 899-905.

V.C. Quee-Smith et al., "Synthesis, Structure, and Characterization of a Novel Manganese(IV) Monomer, [MnIV(Me3TACN)(OMe)3](PF6) (Me3TACN=N,N',N"-Trimethyl-1,4,7-triazacyclononane), and its Activity toward Olefin Oxidation with Hydrogen Peroxide", Inorganic Chemistry (1996) vol. 35, No. 22, 6461-6465.

V.B. Romakh et al., "Dinuclear Manganese Complexes Containing Chiral 1,4,7-Triazacyclononane-Derived Ligands and Their Catalytic Potential for the Oxidation of Olefins, Alkanes, and Alcohols", Inorganic Chemistry (2007) vol. 46, No. 4, 1315-1331.

J.Y. Ryu et al., "Alkane Oxidation Catalyzed by Manganese-tmtacn Complexes with H2O2", Bull. Korean Chem. Soc., (2003) vol. 24, No. 12, 1835-1837.

D.C. Sherrington et al., "Polymer-Supported Mo and V Cyclohexene Epoxidation Catalysts: Activation, Activity, and Stability", Journal of Catalysis (1991) vol. 131, 115-126.

G.B. Shul'pin et al., "Oxidations by the system 'hydrogen Peroxide-[Mn2L2O3][PF6]2 (L=1,4,7-trimethyl-1,4,7-triazacyclononane)-oxalic acid'. Part 6. Oxidation of methane and other alkanes and olefins in water", Journal of Organometallic Chemistry 690 (2005) 4498-4504.

G.B. Shul'pin et al., "Oxidation with the 'H2O2-maganese(IV) complex-carboxylic acid' reagent", Russian Chemical Bulletin (1998) vol. 47, No. 12, 2379-2386.

K.F. Sibbons et al., "The application of manganese complexes of ligands derived from 1,4,7-triazacyclononane in oxidative catalysis" Dalton Translation (2006) 645-661, The Royal Society of Chemistry, Cambridge, England.

C. Venturello et al., "A New, Effective Catalytic System for Epoxidation of Olefins by Hydrogen Peroxide Under Phase-Transfer Conditions", Journal of Organic Chemistry (1983) vol. 48, No. 21, 3831-3833, American Chemical Society, Easton.

C.B. Woitiski et al., "Oxidations by the system 'hydrogen peroxide-dinuclear manganese(IV) complex-carboxylic acid' Part 5. Epoxidation of olefins including natural terpenes", Journal of Molecular Catalysis A: Chemical 222 (2004) 103-119.

P. Wu et al., "A novel titanosilicate with MWW structure Catalytic properties in selective epoxidation of dialyl ether with hydrogen peroxide" Journal of Catalysis 228 (2004) 183-191.

Z. Xi et al., "An Environmentally Benign Route for Epochlorohydrin From Allyi Chloride Epoxidation Catalyzed by Heteropolyphophatolungstate", Research on Chemical Intermediates (2007) vol. 33 No. 6, 523-534. VSP.

J.W. de Boer, "Mechanism of Cls-Dehydroxylation and Epoxidation of Alkenes by Highly H2O2 Efficient Dinuclear Managanese Catalysts." with Online Supporting Information, Inorganic Chemistry (2007), vol. 46, No. 16, pp. 6353-6372, American Chemical Society.

* cited by examiner

PROCESS FOR THE MANUFACTURE OF A 1,2-EPOXIDE

RELATED APPLICATION DATA

This application claims the benefit of PCT Application PCT/EP2009/004977 with an International Filing Date of Jul. 9, 2009, published as WO2010/012361, which PCT Application PCT/EP2009/004977 further claims priority to European Patent Application No. EP08075680.2 filed Aug. 1, 2008, the entire contents of both are hereby incorporated by reference.

TECHNICAL FIELD

The invention relates to a process for the manufacture of a 1,2-epoxide by catalytic oxidation of the corresponding terminal olefin using hydrogen peroxide and a manganese complex.

BACKGROUND ART 1,2-Epoxides are valuable intermediates, especially when the molecule contains a second functional group. Thus, epoxides as a whole are a very important class of compounds as starting materials for polymers and as intermediates in the organic synthesis. Conventionally, these epoxides are prepared with the use of epichlorohydrin.

The catalytic oxidation of olefins by hydrogen peroxide has seen increased patent activity and has drawn quite some academic interest, although actual use of these oxidation reactions has not seen a commercial follow-up.

For instance the process for the manufacture of epichlorohydrin ("ECH") in WO2004/048353 is carried out in a reaction medium comprising at least 75% w of organic material, causing significant isolation problems.

As mentioned above, epoxidation of terminal or electron-deficient olefins with hydrogen peroxide catalyst by manganese catalysts has been extensively described in the public art, but typically using acetonitrile as reaction medium. An example of such a paper is Tetrahedron Letters 43 (2002) 2619-2622, with turnover numbers of up to 860. In the oxidation of ethylbenzene, in Journal of Molecular Catalyst A: Chemical 185 (2002) 71-80, a mixture of acetonitrile and water is used. In Journal of Oganometallic Chemistry 520 (1996) 195-200 a series of manganese complexes are explored on their catalytic behavior using different solvents. Water was not studied. A heterogenized Mn catalyst has been described in *Angew. Chem. Int. Ed.*, 1999, 38, No. 7, using acetone and acetonitrile as solvents. In Bull. Korean Chem. Soc., 2003, Vol. 24, No. 12, 1835 the alkane oxidation catalyzed by manganese tmtacn complexes with hydrogen peroxide is described, using acetone as solvent. The oxidation of saturated hydrocarbons is described in Russian Chemical Bulletin, Vol. 47, No. 12, December 1998, 2379, using acetonitrile as solvent. The oxidation of alkanes is performed in Inorg. Chem., 2007, 26, 1315-1331 in aqueous nitrile (50%) or in acetone as solvent). The epoxidation of dec-1-ene with hydrogen peroxide in the presence of a dinuclear manganese derivative carried out in a biphasic system provided no epoxide, but in the presence of a small amount of acetonitrile yielded epoxide with a TON of 373, see Journal of Organometallic Chemistry 690 (2005) 4498-4504. In Adv. Synth. Catal. 2002, 344, 899-905 a table is provided on systems based on Mn-TACN derivatives as catalyst for oxidations of organic compounds with hydrogen peroxide. The solvent typically is acetone or acetonitrile, albeit that water has been mentioned for bleaching of stains or oxidation of phenols, which is believed to generate a wide range of products but little or no epoxides. The conclusion of this paper once again seems to be that acetonitrile as a solvent is required. From the same author, G. B. Shul'pin et al, there are a number of papers with the same conclusion on acetonitrile as solvent (Journal of Molecular Catalysis A: Chemical 222 (2004) 103-119). In the paper Inorg. Chem. 1996, 35, 6461-6465 the activity of new manganese catalysts was described towards olefin oxidation with hydrogen peroxide. Interestingly, the olefin oxidation studies showed that oxidation reactions in aqueous solutions of water-soluble olefins did not necessarily result in the corresponding epoxide. For instance, diols were produced when the corresponding epoxide was not sufficiently stable under the reaction conditions. This, however, is not problematic at all if the purpose of the reaction is to bleach stains and either discolor and/or remove contaminants from fabrics by improving their solubility. The mechanism of bleaching has in fact been further studied in Journal of Molecular Catalysis A: Chemical 251 (2006) 150-158. Thus, in alkaline aqueous solutions, typically employed in detergents, the dinuclear species used as catalyst yields lignin oxidation. Again, it should be noted that this process does not seem to be one suitable for actually producing epoxides.

A fairly early paper on the topic of epoxidation suggests the use of water as a solvent; see Tetrahedron Letter 39 (1998) 3221-3224, but all reactions are actually carried out in acetonitrile.

Whether epoxides may be manufactured in water as a solvent, and moreover in high turnover numbers therefore remains unclear.

In EP0618202 the epoxidation of olefins via certain manganese complexes is described. The method is said to include a step of recovering epoxidized olefin. According to this reference, epoxidation is best conducted in a fluid medium, especially an aqueous system. When the epoxidation is conducted in an aqueous medium, it is said that the best results are obtained on olefins with water-soluble groups such as those with carboxylate and hydroxyl units, e.g., vinylbenzoic acid, styrylacetic acid, and hexenoic acid which are all fully soluble in water. In addition to these water-soluble olefins also allyl alcohol is epoxidized using water as reaction medium. Allyl alcohol is completely miscible in water. A further listing of suitable olefins is provided, albeit that these are not the olefins to be used in an aqueous medium. The catalyst:olefin:hydrogen peroxide ratio in the examples is typically 1:100:10,000, which corresponds with the (preferred) ratio of oxidizing agent in relation to the olefin of from 500:1 to 20:1. Interestingly, no data is provided on the yield of epoxide, which rather suggests that the olefin is not only converted into the corresponding epoxide but also (or more so) in the corresponding diol, as might be expected on the basis of the academic studies reported on earlier in this specification.

From the above it is clear the industry is still looking for a commercially feasible process for the manufacture of 1,2-epoxides, in high turnover numbers and at high selectivity, meaning substantially free of byproducts such as diols. This process should also allow the use of an aqueous solvent as reaction medium, to avoid environmental and other problems related to acetonitrile and similar organic solvents. The present invention overcomes these disadvantages.

DISCLOSURE OF THE INVENTION

Accordingly, the invention provides a process for the manufacture of a 1,2-epoxide by catalytic oxidation of a terminal olefin with hydrogen peroxide wherein the catalytic oxidation is performed in a biphasic system comprising an organic phase and an aqueous reaction medium, wherein a water-soluble manganese complex is used as oxidation catalyst, wherein a terminal olefin is used with a limited solubility at 20° C. of at least 0.01 to 100 g in 1 liter water, and wherein the molar ratio of terminal olefin to hydrogen peroxide is in the range of from 1:0.1 to 1:2.

MODE(S) FOR CARRYING OUT THE INVENTION

As used in the current specification, the expressions epoxidation and oxidation refer to the same reaction; the conversion of a carbon-carbon double bond into an oxirane ring. Oxidation and epoxidation may also result in the preparation of diols and other derivatives, for instance in case of bleaching, but such is considered undesirable in the context of the present invention.

The invention is hereafter discussed in greater detail.

In terms of water-soluble manganese complexes that may be used as oxidation catalyst, many suitable complexes are known. Typically the catalyst comprises a manganese atom or a number of manganese atoms coordinated with a ligand or ligands. The manganese atom(s) may be in a II, III or IV oxidation state and be activated during the reaction. Of particular interest are binuclear manganese complexes, such as those described in the open and patent literature described in the introductory part of this patent application. Suitable manganese complexes therefore include mononuclear species of the general formula (I):

and binuclear species of the general formula (II):

wherein Mn is a manganese; L or each L independently is a polydentate ligand, preferably a cyclic or acyclic compound containing 3 nitrogen atoms; each X independently is a coordinating species and each μ-X independently is a bridging coordinating species, selected from the group consisting of: $RO^-$, $Cl^-$, $Br^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, wherein R is a $C_1$-$C_{20}$ radical selected from the group consisting of alkyl, cycloalkyl, aryl, benzyl and combinations thereof, and Y is an oxidatively-stable counterion. Counterion Y may for instance be an anion selected from the group consisting of $RO^-$, $Cl^-$, $Br^-$, $I^-$, $F^-$, $SO_4^{2-}$, $RCOO^-$, $PF_6^-$, acetate, tosylate, triflate ($CF_3SO_3^-$) and a combination thereof with R once again being a $C_1$ to $C_{20}$ radical selected from the group consisting of alkyl, cycloalkyl, aryl, benzyl and combination thereof. The type of anion is not very critical, although some anions are more preferred than others. A preferred counterion is $PF_6^-$. Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). The prefer ligand is 1,4,7-trimethyl-1,4,7,-triazacyclononane ("TmTacn"), which is commercially available from for instance Aldrich. In this respect it is important to note that the water-solubility of the manganese catalyst is a function of all the aforementioned catalyst components. For instance, a mononuclear manganese complex prepared from MNSO4 and TmTacn was found to be insufficiently soluble.

Dinuclear manganese complexes are preferred, because of their greater activity and solubility in water. Preferred dinuclear manganese complexes are those of the formula $[Mn^{IV}_2(\mu\text{-O})_3L_2]Y_2$, wherein L and Y have the meaning identified above, preferably TmTacn as ligand, and $PF_6^-$ or acetate ($CH_3CO_2^-$, hereinafter OAc) as counterion.

According to the present invention, the manganese complex may be utilized directly or as adsorbed onto a solvent insoluble support surface. Illustrative but nonlimiting examples of such substrates are structured aluminosilicates (e.g. Zeolite A, faujasite and sodalite), amorphous aluminosilicates, silica, alumina, charcoal, microporous polymeric resins (e.g. polystyrene beads formed through high internal phase emulsion technology) and clays (especially layered clays such as hectorite and hydrotalcite). Relative weight ratios of the manganese complex to the support may range anywhere from about 10:1 to about 1:10,000.

The manganese complex is used in catalytically effective amounts. Typically, the catalyst is used in a molar ratio of catalyst (Mn) versus the terminal olefin of from 1:10 to 1:10,000,000, preferably of from 1:20 to 1:100,000, most preferably of from 1:50 to 1:1000. As a matter of convenience the amount of catalyst may also be expressed in terms of its concentration, when keeping in mind the volume of the aqueous medium. For instance, it may be used in a molar concentration (based on the Mn) of from 0.001 to 10 mmol/L, preferred of from 0.01 to 7 mmol/L and most preferably of from 0.01 to 2 mmol/L. In this respect it is also important to note that the epoxidation is first order on the catalyst concentration and proportional to the catalyst amount. With increase in the catalyst amount, the activity increases. The higher amounts, however, need to be balanced by the higher cost.

The aqueous reaction medium typically is a water phase containing the dissolved epoxide and/or terminal olefin and less than 25% by volume, preferably only minor amounts, if any of other organic compounds. Although not preferred, the reaction medium may contain minor amounts of co-solvents such as methanol and acetone and the like. Whilst excluding the presence of the epoxide and/or terminal olefin, the aqueous reaction medium suitably comprises at least 90% by volume of water, preferably 95% v, more preferably 99% v, still more preferably 99.9% v of water. Most preferably, however, the aqueous reaction medium is essentially a 100% water phase.

The aqueous reaction medium may contain a buffer system so as to stabilize the pH. For instance, it has been found that the aqueous reaction medium is suitably stabilized in a pH range of 2.5 to 8, whereas the preferred pH range is between 3 and 7 and the most preferred is between 3.5 to 6.5. The pH is therefore (well) below that used when bleaching olefins, typically carried out at more alkaline conditions (e.g., pH adjusted with $NaHCO_3$ to 9.0). The suitable or preferred range may be achieved by several known acid-salt combinations, with the preferred combination being based on oxalic acid-oxalate salt. When oxalic acid and sodium oxalate are used, the pH ratio may be varied from 3.7 to 4.2. Typically, this buffer may be used in a molar ratio to the catalyst of about 10:1, but the amounts may be varied broadly, e.g., ranging from 1:1 to 100:1.

The aqueous reaction medium may also contain a phase transfer agent and/or a surfactant, in particular if a terminal olefin is used with low solubility (e.g., below 0.1 g/L water). Known phase transfer agents that may be used in the process of the invention include quaternary alkyl ammonium salts. Known surfactants that may be used in the process of the invention include non ionic surfactants such as Triton X100™ available from Union Carbide.

The reaction conditions for the catalytic oxidation may be quickly determined by a person skilled in the art. Pressure is not of particular relevance. The reaction is exothermic, and cooling of the reaction medium may be required. The reaction is preferably carried out at temperatures anywhere from −5° C. to 30° C., preferably from 0° C. to 20° C., and most preferably from 0° C. to 10° C.

Of particular importance in the process of the current invention is that the process is carried out in a biphasic system, which definition includes multiphasic systems in case the 1,2-epoxide and the terminal olefin form separate phases. Because the reaction is carried out in a biphasic system, using a terminal olefin with a limited solubility as defined hereinafter, moreover at the right molar ratio of hydrogen peroxide versus terminal olefin, the inventors have achieved producing the corresponding 1,2-epoxide at high turnover numbers, with high selectivity towards the 1,2-epoxide with moreover improved ease of isolating the produced 1,2-epoxide. The biphasic system is created by adding the terminal olefin (as reactant) in an amount greater than what dissolves in the reaction medium. The biphasic system may also be created by conversion of the terminal olefin into the corresponding 1,2-epoxide, which then separates from the reaction medium and forms the organic phase. To ensure optimal results, the addition of reactants should be to the aqueous medium and in case of mixing, back-mixing of the produced 1,2-epoxide should preferably be avoided, if possible. By way of example, the conversion of allyl chloride ("AC") into epichlorohydrin is discussed hereinafter, which in fact may result in a three layer system comprising an organic phase at the bottom, believed to be rich in ECH, whereas it also comprises an organic phase on top that is rich in the starting allyl chloride. In this case the mixing or stirring of the system should preferably be such as to leave the bottom layer substantially undisturbed.

Once again, to have the reaction carried out in a biphasic system, the terminal olefin should have at most limited solubility in the aqueous reaction medium. Outside the scope of the current invention are therefore 4-vinylbenzoic acid, styrylacetic acid, trans-3 or trans-2-hexenoic acid or allyl alcohol as used in the aforementioned EP0618202, since they all are soluble in water. Quite surprisingly, the current inventors actually found a greater production of 1,2-epoxide at higher turnover numbers when using allyl chloride or allyl acetate as compared to allyl alcohol, even though the former have only limited solubility, whereas the latter is fully miscible with water. On the other hand, some solubility is required; conversion of unsubstituted α-olefins (like 1-octene) cannot be achieved by the process of the current invention. Suitable terminal olefins hence have a solubility (expressed in grams per liter water at 20° C.) in the range of from 0.01 to 100 g/L, more preferably from 0.1 to 50 g/L, most preferably from 0.5 to 20 g/L. Examples of suitable terminal olefins include halogenated olefins having from 3 to 8 carbon atoms in the molecule, hydroxyl-substituted olefins having 4 to 6 carbon atoms in the molecule, carbonyl-substituted olefins having 3 to 6 carbon atoms in the molecule, alkoxy-substituted olefins having 3 to 8 carbon atoms in the molecule, alkenoic acids having 7 to 8 carbon atoms and esters of alkenoic acids having in total 4 to 8 carbon atoms, allyl esters of alkanoic acids having 3 to 8 carbon atoms, etc. Of particular (commercial) relevance are allyl bromide (solubility of 4 g/L), allyl chloride (solubility of 3.6 g/L), and allyl acetate (solubility of about 10 g/l). Also suitable and of approximately the same solubility are allyl priopionate, allyl butanoate, allyl hexanoate, allyl octanoate, allyl decanoate, allyl stearate, allyl palmitate, allyl salicylate, allyl lactate, and allyl succinate. Preferred terminal olefins are allyl chloride (because of the commercial interest and ease of isolating the product, as discussed hereinafter) and allyl acetate. In addition to the mono-olefins mentioned above, also di-olefins such as for instance diallyl glutarate, diallyl adipate, diallyl pimelate, diallyl oxalate, diallyl maleate, diallyl phthalate and diallyl isophthalate may be used.

The catalytic oxidation of the present invention is carried out using hydrogen peroxide as oxidant. Other oxidants may be used, i.e. as precursor to the hydrogen peroxide, but given the availability and to reduce environmental impact hydrogen peroxide is the preferred oxidant. Hydrogen peroxide has strong oxidizing properties. As bleaching agent it is mostly used for bleaching paper. It is typically used in an aqueous solution. The concentration of hydrogen peroxide may vary, from 15% (e.g., consumer grade for bleaching hair) to 98% (propellant grade), with a preference for industrial grades varying from 20 to 60%, preferably from 30 to 50%.

The molar ratio of terminal olefin to hydrogen peroxide is very important in the process of the current invention. If too much hydrogen peroxide is used, then the selectivity towards the 1,2-epoxide reduces due to the production of undesirable side-products. If not enough hydrogen peroxide is used, then the turnover number is suboptimal. This is therefore significantly different from bleaching conditions described in the prior art, where excessive amounts of hydrogen peroxide are used. The molar ratio of terminal olefin to hydrogen peroxide is in the range of from 1:0.1 to 1:2, more preferably from in the range of from 0.5:1 to 1.2:1 and most preferably about 1:1. To ensure optimal peroxide efficiency, the hydrogen peroxide is preferably added to the aqueous reaction medium at a rate about equal to the reaction rate of the catalytic oxidation.

The catalytic oxidation may be performed in a batch process, in a continuous process or in a semi-continuous process. Indeed, the process may be modified in various aspects without departing from the gist of the invention.

By way of general example the catalytic oxidation of allyl chloride is described hereafter.

The catalytic oxidation may be performed in a common continuous stirred tank reactor, with means of stirring provided extending, for instance, from the top partway to the bottom, leaving a bottom zone which will contain the organic phase rich in ECH, mostly undisturbed. For instance, this may be an elevated, common blade agitator operating under an agitation speed of around 250 rpm in a batch reactor. The catalyst, aqueous reaction medium and reactants may be added in batch, or the reactants may be added over a period of time. As a result of the process of this invention, ECH is formed as a separate bottom layer, which can be removed with ease either at the end of the (bath) reaction or continuously. If hydrogen peroxide is added during the reaction, then it is added to either the (stirred) organic phase comprising the allyl chloride or the (stirred) aqueous reaction media.

In (semi)continuous operations, various recycling streams may be used to control the reaction conditions (maintained at a temperature of between −5° C. and 10° C.) and to optimize the production rate.

In terms of process design, a settler may be added to optimize the gravitational separation of the ECH. Likewise, a membrane unit may be used to recycle the aqueous reaction medium with reduced loss of catalyst.

On example of a mass balance for the reaction process according to the invention is:

| | |
|---|---|
| ECH | about 11 000 kg/h |
| AC | about 9 100 kg/h |
| $H_2O_2$(35%) | about 6 457 kg/h |
| $H_2O$ | about 2 140 kg/h |

As a result of this mass balance, the ratio ECH/cat is about 8000 mol/mol.

The following examples will more fully illustrate selected embodiments of this invention. All parts, percentages and proportions referred to herein and in the appended claims are by weight unless otherwise indicated.

EXAMPLES

Example 1

The catalytic oxidation was carried out with a catalyst of the formula:

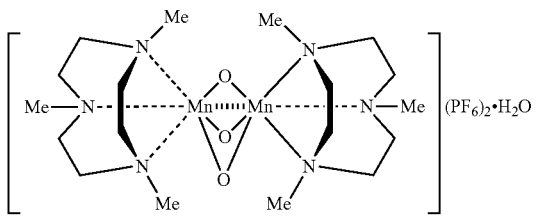

Also used is an oxalate/oxalic acid buffer, with 35% aqueous $H_2O_2$ as oxidant, and water as aqueous reaction medium. The experiment is carried out with allyl chloride as the terminal olefin.

Experimental:

In a typical epoxidation reaction 0.0093 mmol of catalyst in 50 mL of water, 112.5 μmol of sodium oxalate in 7.5 mL of $H_2O$ and 112.5 μmol of oxalic acid in 7.5 mL of $H_2O$ were taken into a three-neck round-bottomed flask equipped with a mechanical stirrer. The reaction started with the addition of olefin (150 mmol) and dilute $H_2O_2$ (200 mmol) at 4° C.

10 mL of extra water was added as solvent for the reaction. The oxidant was added under flow conditions with 8.8 mL/hr into the reaction solution. The pH of the reaction solution was 3.5 to 3.6 and the stirring rate was maintained at 210 rpm for the most of the experiments with mechanical stirrer.

Results and Discussion

The manganese complex produced ECH efficiently using water as solvent. During the epoxidation using water as solvent, at the beginning of the reaction, AC is present as a separate layer on top of the aqueous catalyst solution. As the epoxidation progressed the ECH (having a higher density) separated at the bottom along with some AC dissolved in it. The reaction system thus formed three phases from top to bottom, organic (mainly AC), an aqueous and a second organic (mainly ECH) phase. At the end of the reaction both the top and bottom organic fractions constituted major amounts of ECH and AC. Minor amounts of AC and ECH were also found in the aqueous fraction.

This example provided a 50% yield of epoxide based on olefin produced at 40% selectivity of peroxide, with 7800 TON. There were no noticeable amounts of diols or other side products produced.

Example 2

Various experiments were carried out in the manner of Example 1. In Table 1 the results of the epoxidation of AC at various stirring rates are presented.

TABLE 1

Epoxidation of AC: Variation of stirring rate

| No. | Time period (h) | Stirring rate (rp--m) | ECH (mmol) | TON (for ECH) |
|---|---|---|---|---|
| 1 | 6 | 650 | 33 | 3500 |
| 2 | 6 | 500 | 36 | 3900 |
| 3 | 6 | 210 | 73 | 7800 |
| 4 | 4 | 210 | 64 | 6900 |
| 5 | 4 | 100 | 37 | 3900 |

This example illustrates that the yield of epoxide increases with the stirring rate until the bottom layer become disturbed.

Example 3

Epoxidation of Various Olefins

Epoxidation reactions of various olefins performed with the above manganese complex have been carried out in the manner described in Example 1. The results are shown in Table 2.

TABLE 2

Epoxidation of various olefins

| No | Olefin (mmol) | Solubility in water (g/L) | Time period (h) | epoxide (mmol) | TON |
|---|---|---|---|---|---|
| 1 | Allyl alcohol | miscible | 8 | 53 | 5700 |
| 2 | Allyl chloride | 3.6 | 8 | 76 | 8100 |
| 3 | Allyl acetate | ~10 | 8 | 137 | 14500 |
| 4 | 1-octene | $2.7 \times 10^{-4}$ | 8 | traces | — |

This example illustrates that the yield of epoxide and the turnover number increases as a result of solubility, provided the solubility remains limited. Experiment Nos. 1 and 4 are comparative.

Example 4

Variation in Catalyst Amount

Epoxidation of allyl acetate was carried out in the manner of Example 1, however, with a variation in catalyst amount. This example illustrates that increased amounts of catalyst leads to increased production of epoxides; hence it is possible to decrease the time period. In the best experiment, allyl acetate was converted at 92% yield into glycidyl acetate (GlAc) in 0.5 hours at 95% efficiency. The results are included in the following Table.

TABLE 3

Epoxidation of allyl acetate: Variation of catalyst amount

| No. | Time period (h) | Catalyst amount (mmol) | Efficiency peroxide (%) | GlAc (mmol) | TON |
|---|---|---|---|---|---|
| 1 | 8 | $9.4 \times 10^{-3}$ | nd | 137 | 14500 |
| 2 | 4 | $9.4 \times 10^{-3}$ | 92 | 122 | 13000 |
| 3 | 2 | $18.3 \times 10^{-3}$ | 99 | 126 | 6800 |
| 4* | 1 | $36.7 \times 10^{-3}$ | 91 | 126 | 3433 |
| 5* | 0.5 | $73.4 \times 10^{-3}$ | 95 | 138 | 1880 |

*olefin:hydrogen peroxide ratio was 1:1.03

Example 5

Effect of pH

In the previous experiments the epoxidation reactions have been performed at low pH around 3.5 to 3.6. Here we show that the catalyst is active in both acidic and basic conditions, that is at pH=2.6 with only oxalic acid present, as well as at pH=8 with only sodium oxalate. These results give evidence that the catalyst system is active in the wide pH range for AC epoxidation.

TABLE 4

Effect pH for epoxidation of allyl chloride

| No. | pH | peroxide consumed (mmol) | mmol of ECH formed in Organic phase | mmol of ECH formed in Aqueous phase | TON ECH | Selectivity of peroxide (%) |
|---|---|---|---|---|---|---|
| 1 | 2.6 | 55 | 15.4 | 7.6 | 2400 | 42 |
| 2 | 8 | 121 | 29 | 19 | 5000 | 39 |

Example 6

Effect of the Counterion

In the previous experiments the epoxidation reactions have been carried out with a catalyst having PF6<"> as counterion. In this experiment the corresponding $[Mn_2(\mu-O)_3TmTacn_2](OAc)_2$ has been used. The catalyst is quite active, albeit that it was found that a double amount of oxalate/oxalic acid buffer was required to produce similar activity to that of the $PF_6$ salt. A preliminary result of the use of this catalyst is shown in Table 5.

TABLE 5

Epoxidation of allyl chloride with $[Mn_2O_3L_2](OAc)_2$

| No. | Time period (h) | Stirring rate (rpm) | ECH (mmol) | TON |
|---|---|---|---|---|
| 1 | 8 | 1000 | 674 | 3100 |

The invention claimed is:

1. A process for the manufacture of a 1,2-epoxide, comprising:
reacting a terminal olefin with an oxidant in the presence of a catalyst, in a biphasic system comprising an organic phase and an aqueous reaction medium, wherein the catalyst comprises a water-soluble manganese complex and the terminal olefin has a solubility at 20° C. of at least 0.01 to 100 g in 1 liter water, and wherein the molar ratio of the terminal olefin to the oxidant is in the range of from 1:0.1 to 1:1, wherein the water-soluble manganese complex comprises a mononuclear manganese complex of the formula (I):

[LMnX$_3$]Y     (I)

or a binuclear manganese complex of the formula (II):

[LMn(μ-X)$_3$MnL]Y$_2$     (II)

wherein Mn is a manganese; L or each L independently is a polydentate ligand; each X independently is a coordinating species and each μ–X independently is a bridging coordinating species, selected from the group consisting of: RO⁻, Cl⁻, Br⁻, I⁻, F⁻, NCS⁻, N$_3$⁻, I$_3$⁻, NH$_3$, NR$_3$, RCOO⁻, RSO$_3$⁻, RSO$_4$⁻, OH⁻, O²⁻, HOO⁻, H$_2$O, SH⁻, CN⁻, OCN⁻, and S$_4$²⁻ and combinations thereof, wherein R is a C$_1$-C$_{20}$ radical selected from the group consisting of alkyl, cycloalkyl, aryl, benzyl and combinations thereof, and Y is an oxidatively-stable counterion.

2. The process of claim 1, wherein each polydentate ligand is independently selected from acyclic compounds having at least 7 atoms in the backbone or cyclic compounds having at least 9 atoms in the ring, wherein each polydentate ligand having 3 nitrogen atoms with the nitrogen atoms separated by at least two carbon atoms.

3. The process of claim 1, wherein a binuclear water-soluble manganese complex is used as the catalyst.

4. The process of claim 1, wherein the catalyst is used in a molar ratio of the catalyst (Mn) to the terminal olefin of from 1:10 to 1:10,000,000.

5. The process of claim 1, wherein the aqueous reaction medium is a water phase.

6. The process of claim 1, wherein the aqueous reaction medium further comprises a buffer system and a pH in the range of from 2.5 to 7.

7. The process of claim 1, wherein the reaction is carried out at temperatures in the range from −5° C. and 30° C.

8. The process of claim 1, wherein the biphasic system is created by adding the terminal olefin in an amount greater than what dissolves in the reaction medium, by conversion of the terminal olefin into the corresponding 1,2-epoxide, or combinations thereof.

9. The process of claim 1, wherein the terminal olefin is one or more olefins having a solubility from 0.01 to 50 g/L.

10. The process of claim 9, wherein the terminal olefin is one or more olefins selected from the group of halogenated olefins having from 3 to 8 carbon atoms in the molecule, hydroxyl-substituted olefins having 4 to 6 carbon atoms in the molecule, carbonyl-substituted olefins having 3 to 6 carbon atoms in the molecule, alkoxy-substituted olefins having 3 to 8 carbon atoms in the molecule, alkenoic acids having 7 to 8 carbon atoms and esters of alkenoic acids having in total 4 to 8 carbon atoms, and allyl esters of alkanoic acids having 3 to 8 carbon atoms.

11. The process of claim 9, wherein the terminal olefin is selected from the group consisting of allyl bromide, allyl chloride, allyl propionate and allyl acetate.

12. The process of claim 1, wherein the oxidant comprises hydrogen peroxide and is used as an aqueous solution in a concentration of from 15% to 98%.

13. The process of claim 1, wherein the oxidant comprises hydrogen peroxide at a molar ratio of the terminal olefin to the hydrogen peroxide in the range of from 1:0.1 to 1.2:1.

14. The process of claim 1, wherein the oxidant is added to the aqueous reaction medium at a rate about equal to the reaction rate.

15. The process of claim 1, wherein the reaction is performed in a batch process, in a continuous process or in a semi-continuous process.

16. The process of claim 9, wherein the terminal olefin is an allyl ester of an alkanoic acid having in total 3 to 8 carbon atoms.

17. The process of claim 9, wherein the terminal olefin is a diolefin.

18. The process of claim 9, wherein the terminal olefin is selected from the group consisting of allyl deconoate, allyl salicylate, diallyl phthalate, and combinations thereof.

19. The process of claim 1, wherein the aqueous reaction medium comprises a 100% aqueous medium excluding any dissolved epoxide and terminal olefin.

20. The process of claim 6, wherein the aqueous reaction medium further comprises a pH in the range of from 2.5 to 6.5.

21. The process of claim 6, wherein the buffer system comprises an acid-salt combination.

22. The process of claim 21, wherein the acid-salt combination comprises oxalic acid-oxalate salt.

23. The process of claim 1, wherein Y is an oxidatively-stable counterion selected from the group consisting of $RO^-$, $Cl^-$, $Br^-$, $I^-$, $F^-$, $SO_4^{2-}$, $RCOO^-$, $PF_6^-$, acetate, tosylate, triflate ($CF_3SO_3^-$) and a combination thereof.

24. The process of claim 1, wherein the terminal olefin comprises one or more terminal olefins selected from the group of halogenated terminal olefins having from 3 to 8 carbon atoms in the molecule, alkenoic acids having 7 to 8 carbon atoms and esters of alkenoic acids having in total 4 to 8 carbon atoms, and allyl esters of alkenoic acids having 3 to 8 carbon atoms.

25. The process of claim 1, wherein the catalyst comprises a mononuclear manganese complex of the formula (I):

$$[LMnX_3]Y \qquad (I)$$

or a binuclear manganese complex of the formula (II):

$$[LMn(\mu-X)_3MnL]Y_2 \qquad (II)$$

wherein Mn is a manganese; L or each L independently is a polydentate ligand; each X independently is a coordinating species and each μ–X independently is a bridging coordinating species, selected from the group consisting of: $RO^-$, $Cl^-$, $Br^-$, $I$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, wherein R is a $C_1$-$C_{20}$ radical selected from the group consisting of alkyl, cycloalkyl, aryl, benzyl and combinations thereof, and Y is an oxidatively-stable counterion;

wherein the aqueous reaction medium further comprises a buffer system with a pH range from 2.5 to 7; and wherein the molar ratio of the terminal olefin to the hydrogen peroxide in the range of from 1:0.1 to 1.2:1.

* * * * *